(12) United States Patent
Bodvarsson

(10) Patent No.: US 10,264,369 B2
(45) Date of Patent: *Apr. 16, 2019

(54) COCHLEAR HEARING DEVICE WITH CABLE ANTENNA

(71) Applicant: Oticon A/S, Smørum (DK)

(72) Inventor: Thorvaldur Oli Bodvarsson, København S (DK)

(73) Assignee: OTICON A/S, Smørum (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/991,657

(22) Filed: May 29, 2018

(65) Prior Publication Data

US 2018/0279060 A1  Sep. 27, 2018

Related U.S. Application Data

(63) Continuation of application No. 15/179,042, filed on Jun. 10, 2016, now Pat. No. 10,009,696.

(30) Foreign Application Priority Data

Jun. 11, 2015  (EP) .................................... 15171717

(51) Int. Cl.
*H04R 25/00* (2006.01)
*A61N 1/372* (2006.01)
(Continued)

(52) U.S. Cl.
CPC ....... *H04R 25/554* (2013.01); *A61N 1/36036* (2017.08); *A61N 1/37223* (2013.01);
(Continued)

(58) Field of Classification Search
CPC ............ H04R 25/554; H04R 2225/021; H04R 2225/51; H04R 2225/63; H04R 2225/67
See application file for complete search history.

(56) References Cited

U.S. PATENT DOCUMENTS

| | | |
|---|---|---|
| 4,207,441 A | 6/1980 | Ricard et al. |
| 4,532,930 A | 8/1985 | Crosby et al. |
| (Continued) | | |

*Primary Examiner* — Brian Ensey
(74) *Attorney, Agent, or Firm* — Birch, Stewart, Kolasch & Birch, LLP

(57) ABSTRACT

A hearing aid device comprising a behind-the-ear part, an at-the-head part, a coupling element, a second antenna, and a wireless interface is disclosed. The behind-the-ear part is adapted for being arranged at an ear of a user and for providing a low frequency signal comprising audio. The at-the-head part is adapted for being arranged at the head of the user. The at-the-head part includes a first antenna adapted to communicate with an implant part comprising at least one cochlear electrode adapted for being arranged in the cochlea in proximity of an auditory nerve of the user. The coupling element couples the behind-the-ear part and the at-the-head part and is adapted for transmitting the low frequency signal comprising audio to the at-the-head part. The second antenna is adapted for communicating at high frequency with an external unit. The wireless interface is adapted for receiving and/or sending data via the second antenna. The at-the-head part is adapted for providing the low frequency signal comprising audio to the at least one cochlear electrode. The at least one cochlear electrode is adapted for converting the low frequency signal comprising audio to an output signal perceivable by a user as sound. The coupling element comprises an electrically conducting element coupled to the wireless interface. The electrically conducting element is at least a part of the second antenna and adapted for transferring the signal comprising audio at a low frequency from the behind-the-ear part to the at-the-head part and for transmitting and/or receiving high frequency signals via the second antenna.

20 Claims, 9 Drawing Sheets

(51) Int. Cl.
 *A61N 1/36* (2006.01)
 *A61N 1/05* (2006.01)
(52) U.S. Cl.
 CPC ........ *A61N 1/0541* (2013.01); *A61N 1/37229* (2013.01); *H04R 25/552* (2013.01); *H04R 2225/021* (2013.01); *H04R 2225/51* (2013.01); *H04R 2225/63* (2013.01); *H04R 2225/67* (2013.01)

(56) References Cited

U.S. PATENT DOCUMENTS

| | | | |
|---|---|---|---|
| 7,646,356 B2* | 1/2010 | Adel | H01Q 1/273 343/767 |
| 8,300,863 B2 | 10/2012 | Knudsen et al. | |
| 9,237,404 B2* | 1/2016 | Ozden | H04R 25/554 |
| 9,446,233 B2 | 9/2016 | Meskens | |
| 2002/0067653 A1* | 6/2002 | Toda | G11C 5/025 365/230.03 |
| 2008/0300658 A1 | 12/2008 | Meskens | |
| 2009/0169038 A1* | 7/2009 | Knudsen | H04R 25/558 381/315 |
| 2010/0030012 A1 | 2/2010 | Meskens | |
| 2012/0041515 A1 | 2/2012 | Meskens et al. | |
| 2014/0185848 A1 | 7/2014 | Ozden | |
| 2014/0214123 A1 | 7/2014 | Janssen et al. | |
| 2015/0078600 A1 | 3/2015 | Rasmussen et al. | |

\* cited by examiner

COCHLEAR HEARING DEVICE WITH CABLE ANTENNA

This application is a Continuation of co-pending application Ser. No. 15/179,042, filed on Jun. 10, 2016, which claims priority under 35 U.S.C. § 119(a) to European Patent Application No. EP 15171717.0 filed on Jun. 11, 2015. Each of the above applications is hereby expressly incorporated by reference, in its entirety, into the present application.

FIELD

The present disclosure relates to a hearing device. More particularly, the disclosure relates to a hearing device with a first antenna for communication with an implant part and a second antenna for communicating at high frequency with an external unit. The hearing device may in particular be a hearing aid, such as of an implantable type.

BACKGROUND

Hearing devices can be adapted for communicating wirelessly with external units or external devices. Therefore hearing devices need some sort of antenna. Nowadays in particular hearing aid devices can comprise an antenna for communicating wirelessly with external devices. When two hearing aid devices are used by a user, for example in a binaural hearing system with one of the hearing aid devices at each ear of the user, each of the hearing aid devices is preferably adapted to transmit a wireless signal to the corresponding hearing aid device arranged at the other ear, e.g., in order to simultaneously change settings of the two hearing aid devices. Such hearing aid devices can also communicate with other external devices, e.g., a tablet pc, a personal computer, a mobile phone, such as a SmartPhone or any other external device that is adapted for wireless communication.

It is known to use wireless technology standards for exchanging data over short distances by using short-wavelength radio transmissions, such as Bluetooth applying the ISM band from 2400-2800 MHz.

Hearing devices, in particular, hearing aid devices are very dense applications. Hence when an antenna is integrated into a hearing aid device there are specific requirements that need to be considered, such as the size and position of the antenna. These specific requirements are particularly relevant for hearing aid devices with implant parts which are implantable into the body of a user and adapted to wirelessly communicate with the external part of the hearing aid device, e.g., for a hearing aid device with a cochlear implant, as these kind of hearing aid devices may comprise two antennas.

Therefore, there is a need to provide a solution for including two antennas in a hearing aid device.

SUMMARY

According to an aspect, a hearing device comprises a behind-the-ear part, an at-the-head part, a coupling element, a second antenna, and a wireless interface. The behind-the-ear part is adapted for being arranged at an ear of a user and for providing a low frequency signal comprising audio. The at-the-head part is adapted for being arranged at the head of the user. The at-the-head part includes a first antenna adapted to communicate with an implant part comprising at least one cochlear electrode adapted for being arranged in the cochlea in proximity of an auditory nerve of the user. The coupling element couples the behind-the-ear part and the at-the-head part and is adapted for transmitting the low frequency signal comprising audio to the at-the-head part. The second antenna is adapted for communicating at high frequency with an external unit. The wireless interface is adapted for receiving and/or sending data via the second antenna. The at-the-head part is adapted for providing the low frequency signal comprising audio to the at least one cochlear electrode. The at least one cochlear electrode is adapted for converting the low frequency signal comprising audio to an output signal perceivable by a user as sound. The coupling element comprises an electrically conducting element coupled to the wireless interface. The electrically conducting element is at least a part of the second antenna and adapted for transferring the signal comprising audio at a low frequency from the behind-the-ear part to the at-the-head part and for transmitting and/or receiving high frequency signals via the second antenna.

The data received or sent via the second antenna can for example be a signal comprising audio, a control signal, settings, or any other kind of information that is typically received by or sent to a hearing device. The hearing device can comprise an input transducer, e.g., a microphone, microphone array or the like arranged at or in the behind-the-ear part for providing the low frequency signal. Low frequency signals comprise frequencies below 1 MHz, in particular in the hearing range of humans, i.e., in the kHz range. The input transducer is preferably adapted for receiving a signal comprising audio from the surrounding environment and for providing the low frequency signal based on the signal received from the surrounding environment. The low frequency signal can also be based on data received via the second antenna. The low frequency signal can for example be a combination of signals received by the input transducer and the second antenna. The hearing device therefore preferably comprises electric circuitry including a digital signal processor (DSP), amplifier, one or more filters, digital-analog-converters (DAC), analog-digital-converters (ADC) and/or the like in order to process and/or amplify signals. The hearing device can for example be a hearing aid device, such as a hearing aid and in particular a cochlear implanted hearing aid. The first antenna can for example be a transmitter coil in wireless communication with a coil arranged in the implant part via electromagnetic coupling for providing signals comprising audio and energy signals. The at-the-head part and the implant part may comprise one or more magnets that allow to mount the at-the-head part on a surface of the head above the implant part. The implant part may also be configured to transmit data collected for example by the cochlear electrodes to the at-the-head part. The cochlear electrodes can be arranged like a piano keyboard with each cochlear electrode corresponding to a frequency band of a signal comprising audio and the auditory nerves, i.e., their endings in contact with the electrodes can send electric impulses provided by the cochlear electrodes to the brain of the user, which can interpret the signals as sound.

The hearing device according to the disclosure allows for arranging a first antenna for wirelessly communicating between the first antenna and an implant part and for arranging a second antenna for wirelessly communicating with an external unit via the second antenna while the size of the hearing device is essentially unchanged, i.e., arranging two antennas in the hearing device essentially does not increase the size of the hearing device. This allows for producing hearing devices with small sizes. In particular hearing aid devices with an at-the-head part wearable at the head and a behind-the-ear part wearable behind the ear of the user can be provided. It is possible to arrange the second antenna within the hearing device in a manner that facilitates effective wireless communication with an external unit or external devices, such as a mobile phone, a SmartPhone, a tablet pc, a personal computer, a computer, another hearing device, a remote control, a wireless relay device adapted to transmit audio signals from another communication application, or the like.

According to another aspect, a method for a wireless receiving and/or sending of data in a hearing device is provided. The hearing device comprises a coupling element, a behind-the-ear part, an at-the-head part, a second antenna, and a wireless interface. The coupling element couples the behind-the-ear part and the at-the-head part of the hearing device. The behind-the-ear part is adapted for providing a low frequency signal comprising audio. The at-the-head part includes a first antenna adapted to communicate with an implant part comprising at least one cochlear electrode adapted for converting the low frequency signal comprising audio to an output signal receivable by a user as sound. The second antenna is adapted for communicating at high frequency with an external unit. The wireless interface is adapted for receiving and/or sending data via the second antenna. The method comprises the following steps. Providing an electrically conducting element in the coupling element. Arranging the behind-the-ear part at an ear of a user of the hearing device. Arranging the at-the-head part at the head of the user. Arranging the at least one cochlear electrode in the cochlea in proximity of an auditory nerve of the user. Receiving and/or sending data via said electrically conducting element serving as at least a part of the second antenna. Providing that the coupling element transmits the signal comprising audio to the at-the-head part in order to provide the signal comprising audio to the cochlear electrode.

The data received or sent via the second antenna can for example be a signal comprising audio, a control signal, settings, or any other kind of information that is typically received by or sent to a hearing device. Communicating from the hearing device to another device e.g. an external device such as a mobile phone, control device or the like, may be performed at high frequency here means at frequencies above 1 MHz and up to 100 GHz, such as 300 MHz to 3 GHz, such as 2 GHz to 2.5 GHz, such as 2400 MHz to 2483.5 MHz. The electrically conducting element serves at least as a part of the second antenna, i.e., the second antenna can also extend into the behind-the-ear part, e.g., into a hollow space inside of the casing. The behind-the-ear part can for example comprise an input transducer adapted for providing a low frequency signal comprising audio. The low frequency signal can also be based on data received via the second antenna.

The method for a wireless receiving and/or sending of data in a hearing device according to the disclosure allows for wirelessly communicating between the first antenna and the implant part comprising the at least one cochlear electrode and wirelessly communicating between the external unit and the second antenna essentially without increasing the size of a hearing device performing the method. Hence for example signals can be received from the external unit at the second antenna and can be transmitted to the at-the-head part via the coupling element. The at-the-head part comprises the first antenna which is used to transmit the signals to the implant part in order to provide the signal to the at least one cochlear electrode. The signals can also be received by an input transducer, e.g., a microphone arranged in the behind-the-ear part. The signals can then be transmitted to the at least one cochlear electrode via the coupling element and the first antenna.

According to yet another aspect, a second method for a wireless receiving and/or sending of data in a hearing device is provided. The hearing device comprises a coupling element, a behind-the-ear part, an at-the-head part, a second antenna, and a wireless interface. The coupling element couples the behind-the-ear part and the at-the-head part of the hearing device. The behind-the-ear part is adapted for providing a low frequency signal comprising audio. The at-the-head part includes a first antenna adapted to communicate with an implant part comprising at least one cochlear electrode adapted for converting the low frequency signal comprising audio to an output signal receivable by a user as sound. The second antenna is adapted for communicating at high frequency with an external unit. The wireless interface is adapted for receiving and/or sending data via the second antenna. The method comprises the following steps. Providing an electrically conducting element in the coupling element. Arranging the behind-the-ear part at an ear of a user of the hearing device. Arranging the at-the-head part at the head of the user. Establishing a connection to the at least one cochlear electrode in the cochlea in proximity of an auditory nerve of the user. Receiving and/or sending data via said electrically conducting element serving as at least a part of the second antenna. Providing that the coupling element transmits the signal comprising audio to the at-the-head part in order to provide the signal comprising audio to the cochlear electrode.

The second method for a wireless receiving and/or sending of data in a hearing device according to the disclosure allows for the same functionalities as the previously presented method. The major difference between both methods is that the second method has a step of establishing a connection to the at least one cochlear electrode. In this case the at least one cochlear electrode is pre-implanted in the cochlea in close proximity to an auditory nerve. The previously presented method instead has a step of arranging the at least one cochlear electrode in the cochlea in proximity of an auditory nerve of the user.

According to another aspect, the hearing device according to the disclosure is used.

The hearing device is preferably used in order to improve the hearing of a user, e.g., in a manner of a hearing aid device, such as a hearing aid and in particular as a cochlear implant hearing aid. The hearing device therefore can receive and send data, e.g., signals comprising audio via the second antenna and receive signals comprising audio via an input transducer arranged in or at the behind-the-ear part in order to provide a low frequency signal comprising audio. The low frequency signal comprising audio can be transferred to the at-the-head part in order to transmit the signal to the implant part via the first antenna. The low frequency signal comprising audio can then be provided to the at least one cochlear electrode in order to stimulate the auditory nerves which allows to provide an output signal to the user perceivable as sound.

The use of the hearing device according to the disclosure allows for wirelessly communicating between the first antenna and the implant part comprising the at least one cochlear electrode and wirelessly communicating between the external unit and the second antenna without increasing the size of the hearing device used substantially or at all.

The at-the-head part may be adapted to be magnetically coupled to the implant part at a distance from the ear of the user. The implant part and the at-the-head part preferably comprise at least one magnet in order to allow for the magnetically coupling. This allows for an arrangement of the implant part and at-the-head part in close proximity to each other. In particular the at-the-head part can be mounted at a surface of the head above the implant part. This allows for an improved transmission of signals, i.e., signals comprising audio and energy signals, between the at-the-head part and the implant part.

The second antenna may be an electrically short antenna. This allows for a reduced space requirement and hence allows for a smaller hearing device.

The first antenna may be configured to communicate with the implant part via mutual induction between coils of the first antenna and the implant part. Preferably at least a part of the first antenna arranged in the at-the-head part is a coil. The implant part comprises a coil in order to receive signals comprising audio and energy signals from the first antenna. This allows for providing energy and signals comprising audio to the implant part without the need of a physical connection through the skull of the head of the user. Hence an opening in the head prone to infections can be avoided.

The coupling element may comprise two balanced wires for transmitting the signal comprising audio to the at-the-head part. Preferably the electrically conducting element comprises the wires. This allows for reduction of external noise when the low frequency signals are transmitted via the two balanced wires are fed into a differential amplifier. The balanced wires can be at least a part of the electrically conducting element acting as at least a part of the second antenna.

The wireless interface may be coupled to the electrically conducting element via a high-pass filter. The wireless interface may be coupled to the high-pass filter via a balun and the high-pass filter may then be coupled to the wires via respective capacitors. The behind-the-ear part may include a low-pass filter in the path of the signal comprising audio, i.e. the low frequency signal. This allows for achieving a relatively good signal quality while only few modifications to pre-existing hearing device designs are necessary. Preferably the balun comprises a transformer and the high-pass filter comprises a capacitor and an inductance. A balun in general is a passive electronic device that converts between balanced and unbalanced electrical signals. The skilled person is well aware of a number of examples of baluns.

The hearing device the wireless interface may be adapted for receiving and/or sending data by means of radio frequency signals in the frequency range of 1 MHz to 100 GHz, such as 300 MHz to 3 GHz, such as 2 GHz to 2.5 GHz, such as 2400 MHz to 2483.5 MHz, such as in the frequency range of 1 MHz to 200 MHz, such as 200 MHz to 400 MHz, such as 400 MHz to 800 MHz, such as 800 MHz to 1500 MHz, such as 1500 MHz to 1800 MHz, such as 1800 MHz to 2100 MHz, such as 2100 MHz to 2200 MHz, such as 2200 MHz to 2400 MHz, such as 2400 MHz to 2500 MHz, such as 2500 MHz to 2800 MHz, such as 2800 MHz to 3000 MHz, such as around 2.4 GHz. Radio frequency signals are considered as high frequency signals used for high frequency communication. The wireless interface is optionally adapted for receiving and/or sending data according to a communication standard, such as Bluetooth. This allows for exchanging data over short distances by using short-wavelength radio transmissions. The Bluetooth communication standard is widely used and hence allows for a good compatibility between different devices. Any other common communication standard for exchanging data over short distances may also be used.

The electrically conducting element constitutes a first part of the second antenna and at least a second part of the second antenna may be arranged in the behind-the-ear part, and a feed point to the second antenna may be between the first and second part of the second antenna. The behind-the-ear part preferably comprises a casing which is at least partly formed as a hook with a hollow inner space. The second part of the second antenna arranged in the behind-the-ear part is preferably at least partly arranged in the hollow inner space of the hook. At least a part of the second antenna arranged in the behind-the-ear part can have a radiation pattern resembling a monopole or wire antenna which has a form that depends on a desired radio frequency. Alternatively or additionally at least a part of the second antenna arranged in the behind-the-ear part can be a loop antenna or at least a part of the second antenna arranged in the behind-the-ear part can be a spiral antenna. A spiral is here to be understood as an Archimedean spiral, a helix or a conic spiral, i.e., the spiral can be a curve that winds around a fixed center point at a increasing or decreasing distance from the point or it can be a three dimensional curve that turns around an axis at a constant or continuously varying distance while moving parallel to the axis. The distance between turns may vary along the spiral, and the variation need not be linear or even present between turns. The spiral may be more or less unevenly distributed in the behind-the-ear part. The part of the second antenna arranged in the behind-the-ear part is preferably coupled to the wireless interface via a balun and/or a matching network which is adapted to match the second antenna to obtain maximum energy transfer to/from the wireless interface at a desired radio frequency. Arranging at least a part of the second antenna in the behind-the-ear part allows for facilitating effective wireless communication with an external device or external unit. It furthermore allows for providing a reliable antenna that can be secured to or embedded into a wall of the behind-the-ear part and in particular a wall of the hook. Arranging at least a part of the second antenna in the behind-the-ear part as a spiral antenna allows the antenna to take up less space than a straight antenna.

At least a part of the second antenna may cover at least a part of the outside surface of the hearing device, preferably of the behind-the-ear part, more preferably of the hook of the behind-the-ear part. The antenna may be an indium tin oxide (ITO) or any other suitable type of antenna. This allows for a further reduction of space needed to include the second antenna into the hearing device. A coating layer may be added to protect the antenna from environmental influence.

The hearing device may be used to wirelessly communicate with an external unit, such as another hearing device. This allows for forming a binaural hearing device system or to exchange data with another external unit in order to improve the functionality of the hearing device. Further, the external device may be a mobile phone or other communication device, e.g. a portable computing device, such as a tablet, a computer or the like, or a stationary device, such as a television or an adaptor for a television, or other devices connected to a television, such as a game console.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
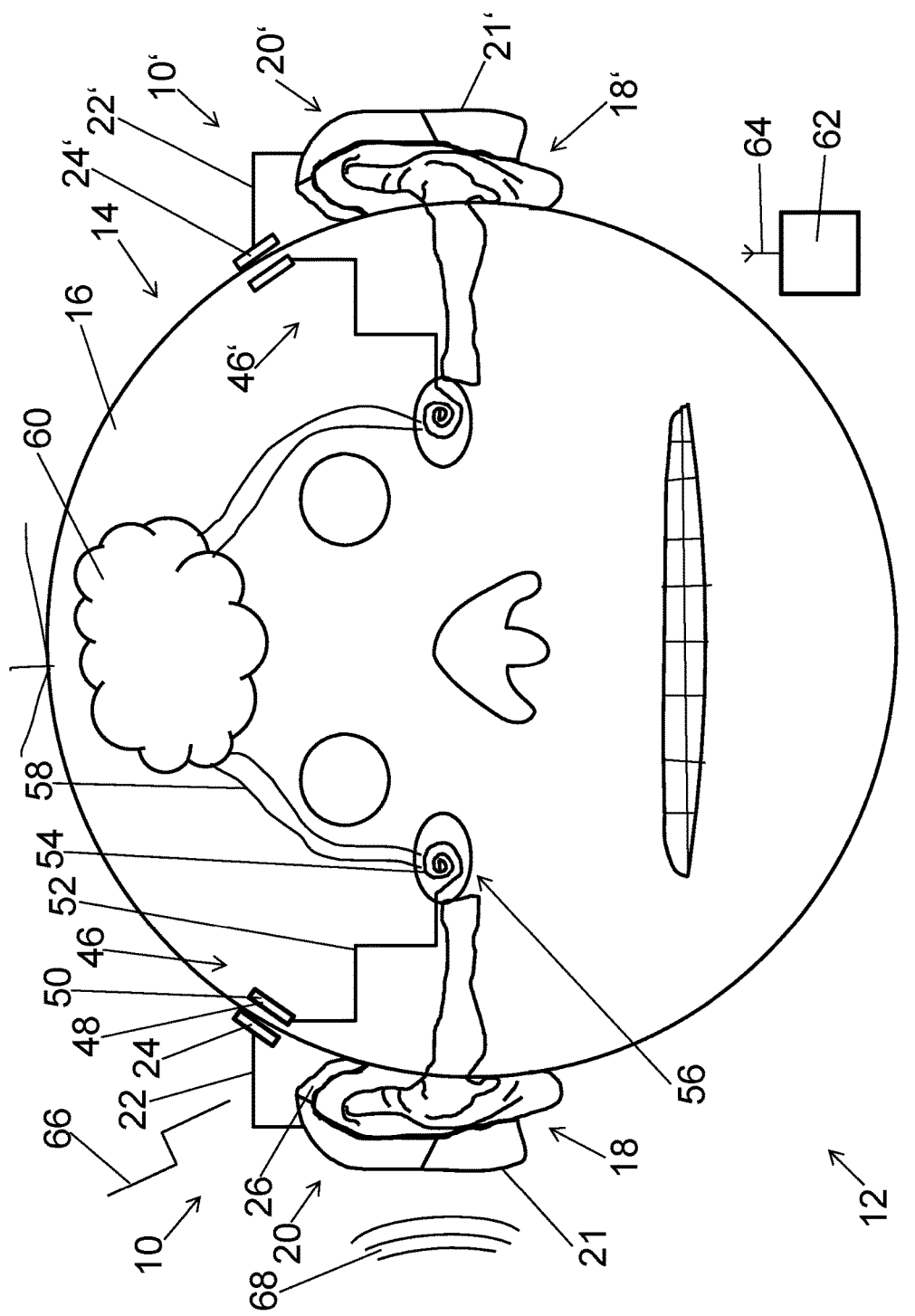
FIG. 1 illustrates a binaural hearing device system comprising two hearing devices worn by a user.

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus or device and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid device or hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears or the corresponding cochlear nerves or auditory nerves associated with the user's ear. The "hearing device" may further refer to a device such as an earphone or a headset adapted to receive an audio signal electronically, possibly modifying the audio signal and providing the possibly modified audio signals as an audible signal to at least one of the user's ears or the corresponding cochlear or auditory nerves associated with the user's ear. Such audible signals may be provided in the form of electric signals transferred directly or indirectly to cochlear nerve and/or to auditory cortex of the user.

The hearing device is adapted to be worn in any known way suitable for a hearing device wirelessly connected with an implant part. This may include i) arranging a unit of the hearing device behind the ear such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Cochlear Implant, or iv) arranging a unit of the hearing device as an entirely or partly implanted unit such as in Cochlear Implant.

A "hearing system" or "hearing device system" refers to a system comprising one or two hearing devices, and a "binaural hearing system" or "binaural hearing device system" refers to a system comprising two hearing devices where the devices are adapted to cooperatively provide audible signals to both of the user's ears or the corresponding cochlear nerves or auditory nerves associated with the user's ear. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, SmartPhones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit, e.g. an input transducer, such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit, e.g., cochlear electrodes for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include one or more output electrodes for providing the electric signals such as in a Cochlear Implant.

A Cochlear Implant as an embodiment of a hearing device typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part or implant part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

FIG. 1 illustrates two hearing devices 10 and 10' according to an aspect of the disclosure of a binaural hearing device system 12 worn by user 14 at his head 16. Hearing device 10 is arranged at the right ear 18 of the user 14 and hearing device 10' is arranged at the left ear 18' or the user 14.

The hearing device 10 comprises a behind-the-ear part 20, a coupling element 22, and an at-the-head part 24. The coupling element 22 couples the behind-the-ear part 20 with the at-the-head part 24. Here, the coupling element 22 is a cable. The coupling element 22 can also for example be a cord, a wire, a lead, or any other kind of coupling element 22.

The hearing device 10' at the left ear 18' comprises the same components as hearing device 10. The components of hearing device 10' are referred to by the same reference signs as the components of hearing device 10 but with an additional prime, i.e., behind-the-ear part 20', coupling element 22' and at-the-head part 24'.

Figure 2:
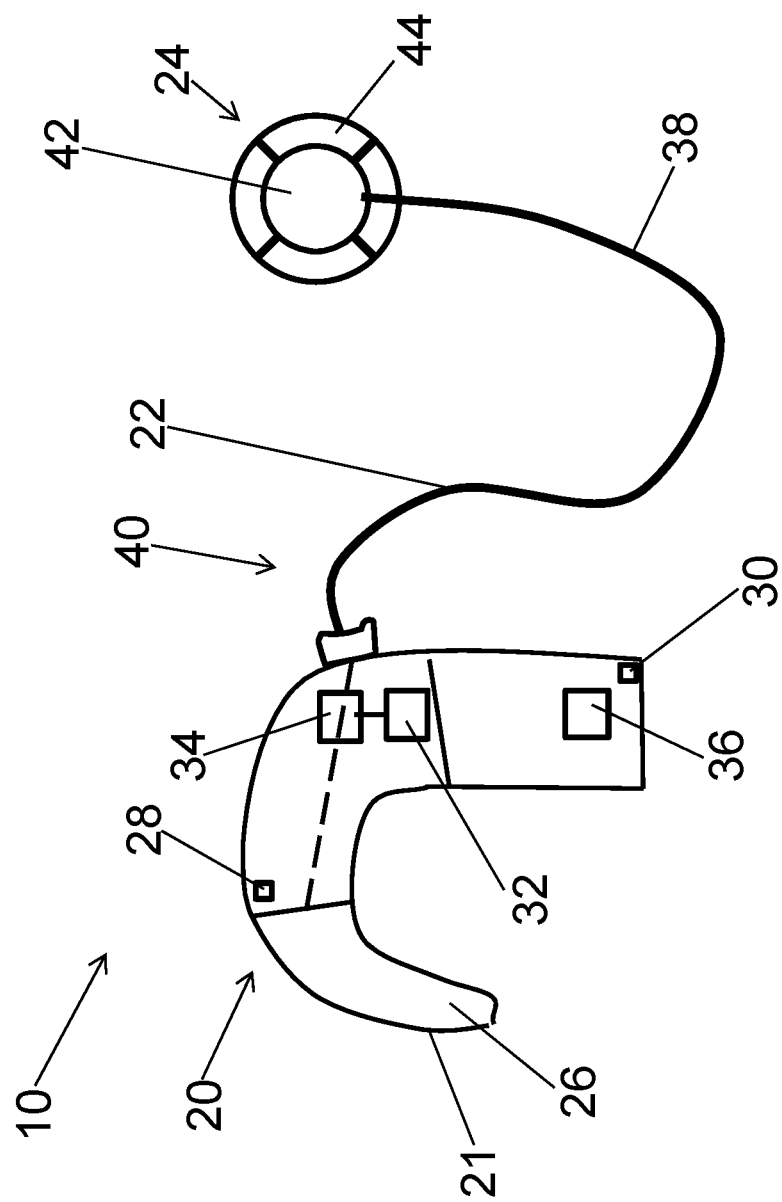
FIG. 2 illustrates a hearing device according to the disclosure.

The behind-the-ear part 20 comprises a casing 21, a hook 26, front microphone 28, back microphone 30, wireless interface 32, electric circuitry 34, and a power source 36 (cf. FIG. 2). The components of the behind-the-ear part 20 are included into casing 21. The hook 26 allows arranging the behind-the-ear part 20 behind the ear 18 of the user 14. The power source 36 is here a battery that powers the hearing device 10. The behind-the-ear part 20 can also comprise only one microphone or a microphone array. Alternative, (although not shown), the behind-the-ear part does not comprise any microphone at all.

The coupling element 22 comprises an electrically conducting element 38 which is coupled to the wireless interface 32. The electrically conducting element 38 comprises two balanced wires that serve as a part of a second antenna 40. The electrically conducting element 38 can also comprise only one wire, three wires, or it can be any other kind of electrically conducting element that can serve as a part of the second antenna 40 and that allows transmitting signals. The second antenna 40 extends over the electrically conducting element 38 and into the behind-the-ear part 20. Here antenna 40 is an electrically short antenna.

The at-the-head part 24 comprises a first antenna 42 in the form of a coil and a magnet 44. The first antenna 42 may also have any other form known to the person skilled in the art that allows electromagnetic coupling. The at-the-head part 24 is arranged at the head 16 of the user 14 at a surface above an implant part 46.

The implant part 46 comprises a coil 48, a magnet 50, a lead 52 and an array of cochlear electrodes 54. The magnet 50 allows mounting the at-the-head part 24 above the implant part 46, as the magnet 50 of the implant part 46 and the magnet 44 of the at-the-head part 24 attract each other if they are in close proximity. Hence the at-the-head part 24 can be magnetically coupled to the implant part 46 at a distance from the ear 18 of the user 14. The lead 52 connects the coil 48 with the cochlear electrodes 54. The cochlear electrodes 54 are arranged in the cochlea 56 of the user 14 in proximity to the cochlear nerves or auditory nerves 58 which carry auditory sensory information from the cochlea 56 to the brain 60.

Accordingly at-the-head part 24' of hearing device 10' is arranged at the head 16 of the user 14 at a surface above implant part 46'.

The binaural hearing device system 12 comprises an external unit 62 with antenna 64. External unit 62 illustrated here is a SmartPhone, but could also be any other kind of external unit that wirelessly communicates with the hearing devices 10 and 10', e.g., a mobile phone, a tablet pc, a personal computer, a computer, a remote control, a wireless relay device adapted to transmit audio signals from another communication application, or the like. Antenna 64 allows the external unit 62 to communicate with the hearing devices 10 and 10' in order to exchange data wirelessly, e.g., settings, signals comprising audio, control signals, alarm signals, or any other kind of data that benefits the user of the hearing devices 10 and 10'. For example music files can be transmitted as wireless signals 66 to both hearing devices 10 and 10'. The external unit 62 can for example use Bluetooth for the wireless transmission.

In the following some basic functions of the hearing device 10 are described with regards to FIG. 1 and FIG. 2. The functionality of the hearing device 10 is not limited to the functions described in the following and the person skilled in the art may imagine various functionalities in view of the components of the hearing device 10.

The front microphone 28 and back microphone 30 of hearing device 10 receive signals 68 comprising audio from the surrounding environment (cf. FIG. 1 and FIG. 2) and provide low frequency signals comprising audio based on the signals 68 received from the surrounding environment. Low frequency signals is preferably viewed as frequencies below 1 MHz, in particular in the hearing range of humans, i.e., in the kHz range. The low frequency signals comprising audio are transferred to the electric circuitry 34.

The second antenna 40 communicates at high frequency with external unit 62 and/or the other hearing device 10'. The wireless interface 32 receives and sends data via the second antenna 40. The second antenna 40 receives high frequency wireless signals 66 comprising data. In particular also the electrically conducting element 38 receives high frequency wireless signals 66 comprising data via the second antenna 40. The second antenna 40 can also transmit high frequency signals comprising data, e.g., a signal derived from the low frequency signals received by microphones 28 and 30. In particular also the electrically conducting element 38 can transmit high frequency signals via the second antenna 40. High frequency here are taken to mean frequencies above 1 MHz, and up to 100 GHz, such as 300 MHz to 3 GHz, such as 2 GHz to 2.5 GHz, such as 2400 MHz to 2483.5 MHz. The wireless signals 66 are also transferred to the electric circuitry 34.

The electric circuitry 34 processes the low frequency signals comprising audio and the wireless signals. The electric circuitry 34 therefore includes analog-digital-converter (ADC), digital-analog-converter (DAC), a signal processing unit, in this case a digital signal processor (DSP), amplifier and filters. The electric circuitry 34 generates a processed signal based on the low frequency signals comprising audio and the wireless signals. The wireless signals may for example comprise a control signal that adjusts the settings of the components of the electric circuitry 34 in order to process the low frequency signal comprising audio and/or a signal comprising audio, e.g., the signal received at the other hearing device 10'. The processed signal thus can also be a combination of a signal comprising audio received by the second antenna 40 and the low frequency signals comprising audio of microphones 28 and 30. Hence the behind-the-ear part 20 provides a low frequency signal comprising audio, i.e. the processed signal. The behind-the-ear part 20 furthermore provides energy signals provided from the power source 36.

The processed signal and the energy signals are provided to the coupling element 22 which couples the behind-the-ear part 20 and the at-the-head part 24. The electrically conducting element 38 included in the coupling element 22 transmits the low frequency signal comprising audio, i.e., the processed signal at a low frequency and the energy signals to the at-the-head part 24.

The first antenna 42 included in the at-the-head part 24 is here a coil that allows to transmit the low frequency signal comprising audio, i.e., the processed signal and the energy signals to the coil 48 arranged in the implant part 46. Hence the first antenna communicates with the implant part 46. Alternatively, (not shown), the coil 48 of the implant part 46 can also transmit data, e.g., status data, sensor data, settings or the like to the first antenna 42 of the at-the-head part 24. The implant part 46 does not need an internal power source due to the energy supply by the energy signals and can be powered externally via electromagnetic coupling, e.g. via precharging or the like.

The low frequency signal comprising audio, i.e., the processed signal is transmitted via lead 52 to the cochlear electrodes 54. The cochlear electrodes 54 are arranged like a piano keyboard in the cochlea 56 with each cochlear electrode 54 corresponding to a frequency band of a signal comprising audio in close proximity to the auditory nerves 58. The cochlear electrodes 54 thus convert the low frequency signal comprising audio to an output signal perceivable by the user 14 as sound. Therefore the auditory nerves 58, i.e., their endings in contact with the electrodes 54 send electric impulses provided by the cochlear electrodes 54 to the brain 60 of the user 14, which can interpret the signals as sound.

The essential function of the binaural hearing device system 12 uses both hearing devices 10 and 10'. In particular both hearing devices 10 and 10' generate low frequency signals comprising audio and exchange the signals via their second antennas 40 and their wireless interfaces 32. The corresponding wireless signals 66 are processed by the electric circuitry 34 of the hearing devices 10 and 10' and corresponding processed signals are provided to the user 14 as described above for some of the functions of the hearing device 10. Various functionalities of the binaural hearing device system 12 are obviously apparent to the person skilled in the art, in particular if the external unit 62 is also included into the wireless communication. For example, an external unit 62 in form of a remote control can be used in order to control the hearing devices 10 and 10' or the binaural hearing device system 12. Hence, the remote control can be used to adjust the volume settings or to activate personalised settings. Personalised settings can for example comprise the amplification of certain frequency bands that the user has problems to hear, as the auditory nerves or cochlear electrodes for that frequency bands might be damaged or misaligned relative to the corresponding auditory nerves.

In the binaural hearing device system 12 presented in FIG. 1 both hearing devices 10, 10' are of the same type, i.e. cochlear hearing aid devices. In an alternative (not shown) the binaural hearing device system 12 could also comprise a hearing device 10 according to an aspect of the disclosure arranged at one of the ears 18 and 18' and another type hearing device, e.g., a Receiver-In-The-Ear (RITE) hearing device, In-The-Ear (ITE) hearing device, Completely-In-The-Canal (CIC) hearing device arranged at the other one of the ears 18' and 18. This is sometimes referred to as a bimodal fitting. The other hearing device would then typically comprise an output unit that include an output transducer such as a loudspeaker/receiver for providing an air-borne acoustic signal transcutaneously or percutaneously to the skull bone or a vibrator for providing a structure-borne or liquid-borne acoustic signal. The other hearing device generates audible signals that may be provided in the form of an acoustic signal radiated into the user's outer ear, or an acoustic signal transferred as mechanical vibrations to the user's inner ears through bone structure of the user's head and/or through parts of middle ear of the user.

In FIG. 1, the hearing device 10 may used to wirelessly communicate with the other hearing device 10' or the external unit 62. It can also be used to wirelessly communicate with both devices.

Hearing device 10 and 10' can also be independently operated without using the binaural functionality. Hence it is also possible to mount only one of the hearing devices 10 and 10' at one of the ears 18 or 18' of the user 14.

Figure 3:
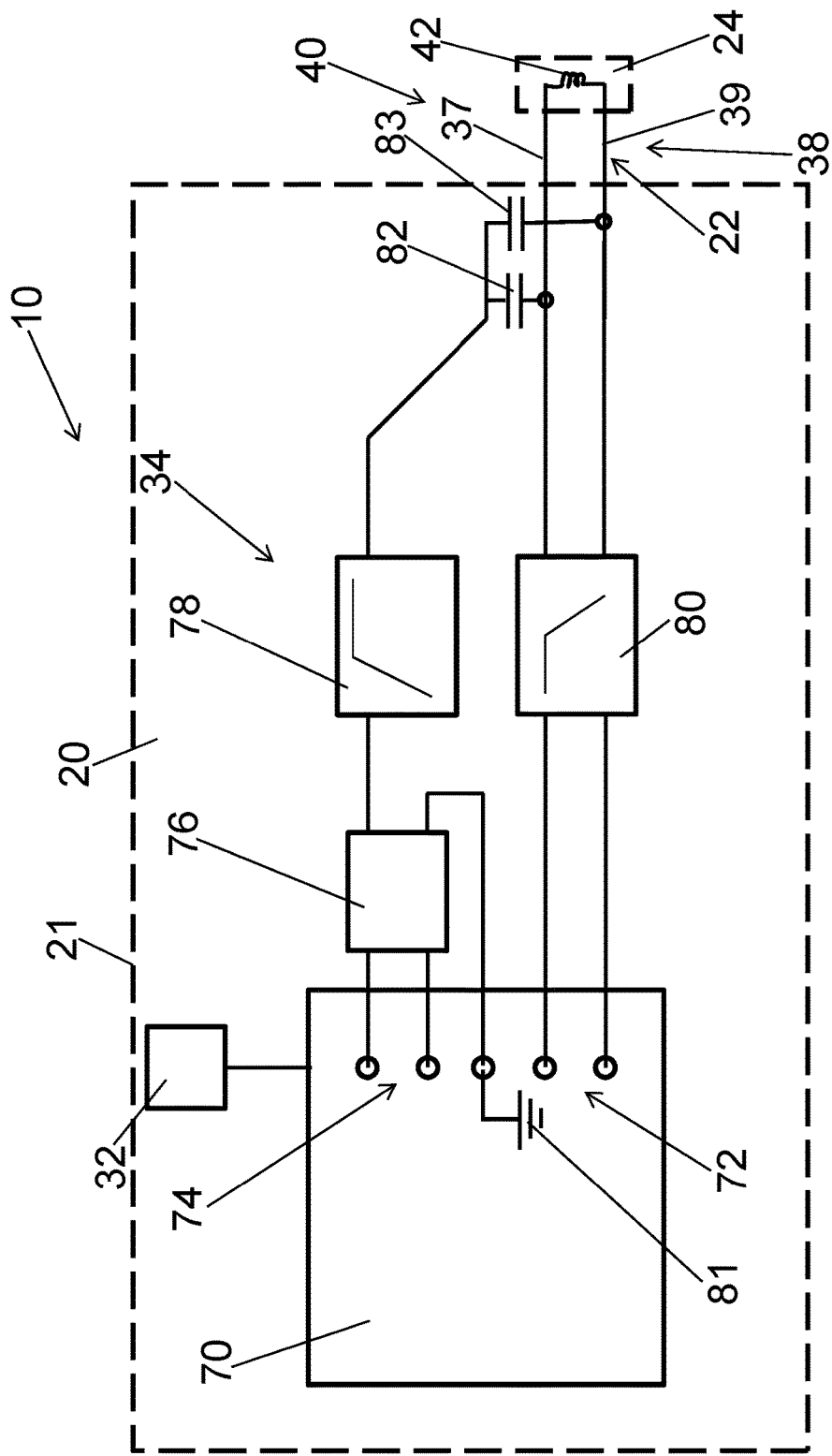
FIG. 3 illustrates a schematic block diagram of a hearing device.

FIG. 3 shows a schematic block diagram of a hearing device 10. The hearing device 10 comprises a behind-the-ear part 20, an at-the-head part 24, a second antenna 40, a first antenna 42, a coupling element 22, and a wireless interface 32.

Here the behind-the-ear part 20 comprises electric circuitry 34 partly in form of a printed circuit board (PCB) 70 for realizing some of the primary features of the hearing device 10, e.g., processing and generating the processed signal to be provided to the user 14. The PCB 70 comprises a signal processing unit for processing signals and is connected to the wireless interface 32. The wireless interface 32 can also be part of the PCB (not shown). The behind-the-ear part 24 further comprises low frequency signal connections 72, high frequency signal connections 74, a balun 76, a high-pass filter 78, and a low-pass filter 80. The low-pass filter 80 is coupled to low frequency signal connections 72 of the PCB 70. The balun 76 is coupled to the high frequency signal connections 74 of the PCB 70. The balun 76 is further coupled to a ground connection 81 and to the high-pass filter 78. The high-pass filter 78 and the low-pass filter 80 are coupled to balanced wire 37 and balanced wire 39 of the coupling element 22. The high-pass filter 78 is coupled to the balanced wires 37 and 39 via capacitors 82 and 83. The balanced wires 37 and 39 are included in the electrically conducting element 38. The low-pass filter 80 is coupled to the first antenna 42 provided in the at-the-head part 24. The first antenna 42 is here a coil which receives low frequency signals comprising audio via the electrically conducting element 38 and provides them to the coil 48 of the implant part 46. High frequency signals to be sent by the second antenna 40 are converted by the balun 76 and passed through the high-pass filter 78, exciting the second antenna 40 including the electrically conducting element 38. In case the second antenna 40 or electrically conducting element 38 is excited by external high frequency signals arriving at the hearing device 10, these external high frequency signals are passed through the high-pass filter 78 and the balun 76 to enter the PCB 70 at the high frequency signal connections 74, where the external signals are received by the wireless interface 32 connected to PCB 70. Hence FIG. 3 illustrates how the high frequency signal or transceiver radio frequency (RF) signal is isolated from the signal comprising audio and connected to two balanced wires. The low-pass filter 80 is provided in series with the audio signal and a high-pass filter 78 is provided in series with the high frequency signal.

Figure 4:
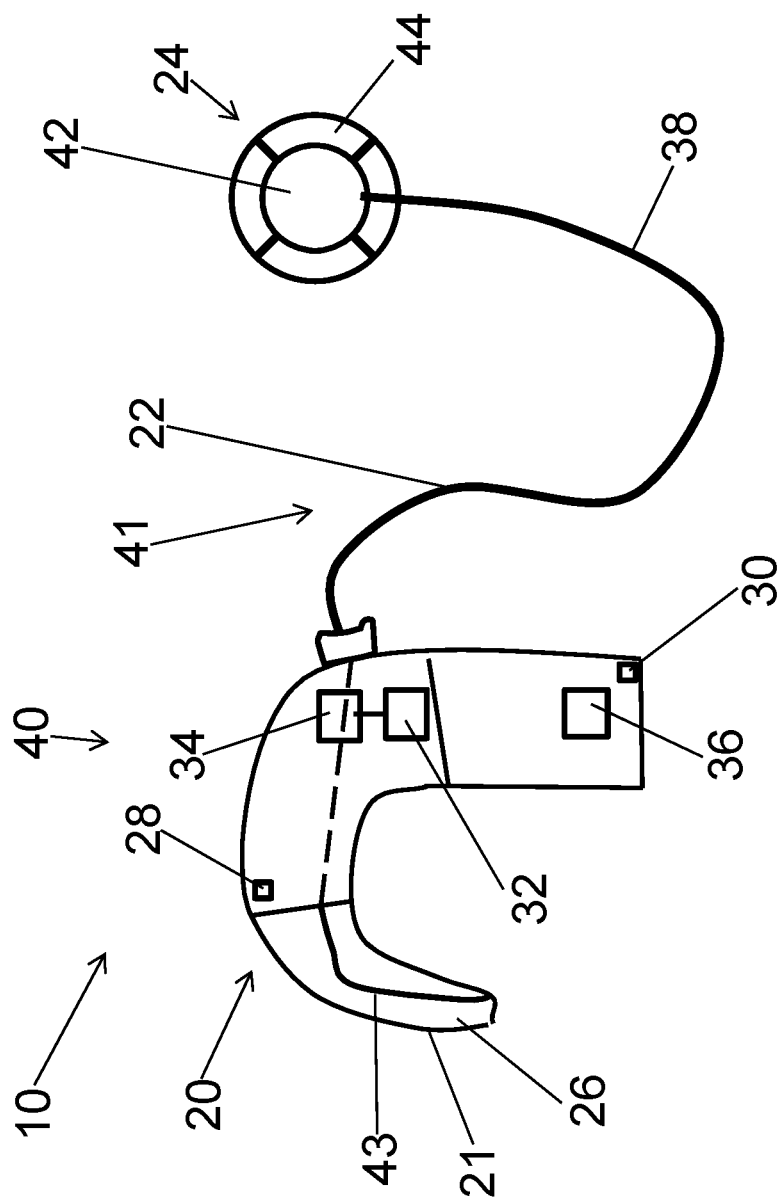
FIG. 4 illustrates a hearing device.

FIG. 4 illustrates a hearing device 10. The hearing device 10 of FIG. 4 is similar to the hearing device according to the hearing device presented in FIGS. 1 and 2. The main difference is that the second antenna 40 of the hearing device 10 shown in FIG. 4 has two second antenna parts 41 and 43. This could be seen as a dipole-like structure where the parts 41 and 43 are fed from inside the housing. The electrically conducting element 38 forms the first antenna part 41. The second antenna part 43 is arranged in the hollow inner space of the hook 26 inside of the behind-the-ear part 20. The second antenna part 43 can also extend over the inner space of the hook 26 into other parts of the behind-the-ear part 20. A feed point to the second antenna 40 is between the first part 41 and second part 43 of the second antenna 40. Here the feed point is arranged in the electric circuitry 34. The second antenna part 43 has a radiation pattern resembling a monopole or wire antenna which has a form that depends on a desired radio frequency. This allows forming a second antenna part 43 that has a desired radio frequency for high frequency signal communication with external units or external devices. The second antenna part 43 of the second antenna 40 is coupled to the wireless interface 32 via a balun (not shown) which is adapted to tune the second antenna 40 to a desired radio frequency. Alternatively a matching network can be arranged between the second antenna part 43 and the wireless interface 32 in order to tune the second antenna 40 to a desired radio frequency.

The wireless interface 32 allows for receiving and/or sending data by means of radio frequency signals in the frequency range of 1 MHz to 100 GHz, such as 300 MHz to 3 GHz, such as 2 GHz to 2.5 GHz, such as 2400 MHz to 2483.5 MHz, such as in the frequency range of 1 MHz to 200 MHz, such as 200 MHz to 400 MHz, such as 400 MHz to 800 MHz, such as 800 MHz to 1500 MHz, such as 1500 MHz to 1800 MHz, such as 1800 MHz to 2100 MHz, such as 2100 MHz to 2200 MHz, such as 2200 MHz to 2400 MHz, such as 2400 MHz to 2500 MHz, such as 2500 MHz to 2800 MHz, such as 2800 MHz to 3000 MHz, such as around 2.4 GHz. The wireless interface 32 can in particular be adapted for receiving and/or sending data according to a communication standard, such as Bluetooth. Hence in the hearing device 10 the second part 43 of the second antenna 40 is formed such that its radiation pattern resembles a wire antenna with a radio frequency corresponding to the ISM band, i.e., from 2400-2800 MHz of the Bluetooth communication standard.

Figure 5:
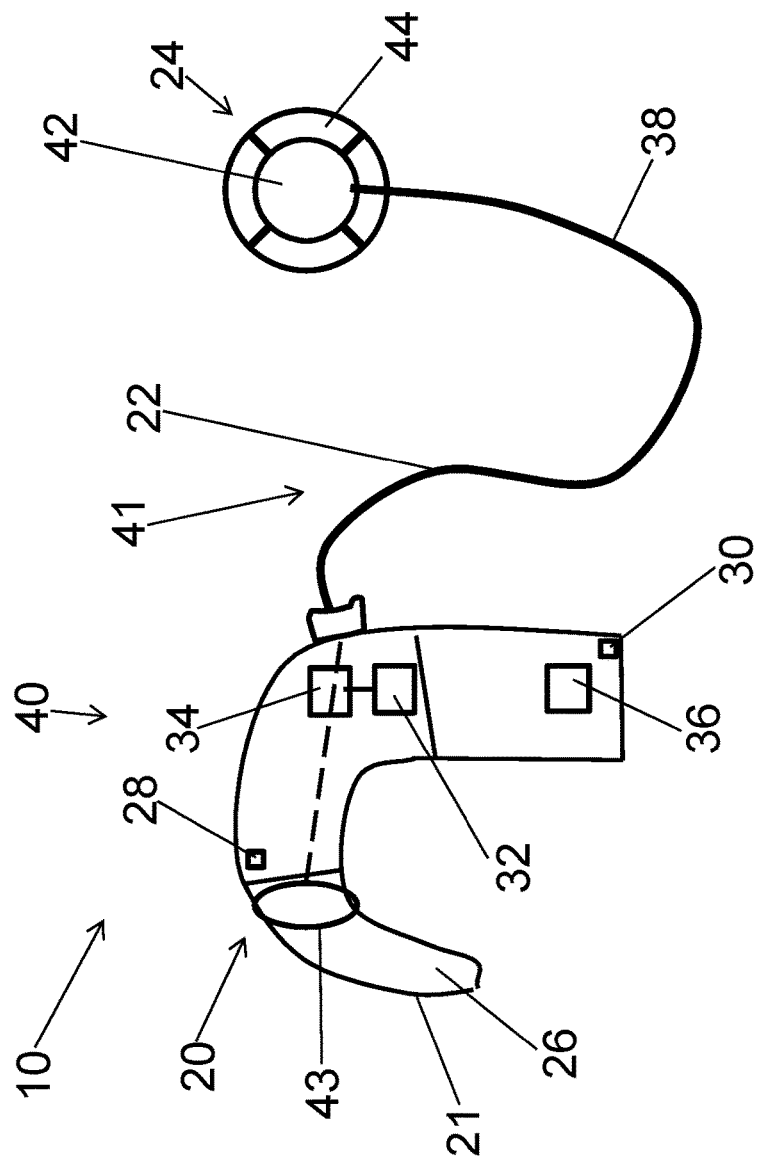
FIG. 5 illustrates a hearing device.

FIG. 5 illustrates a hearing device 10. The hearing device 10 is similar to the hearing device 10 presented in FIG. 4. The hearing device 10 in FIG. 5 also has two second antenna parts 41 and 43 of the second antenna 40. The main difference is that the part of the second antenna 40 arranged in the behind-the-ear part 20 is a loop antenna. In particular the second part 43 of the second antenna 40 is arranged in hook 26.

Figure 6:
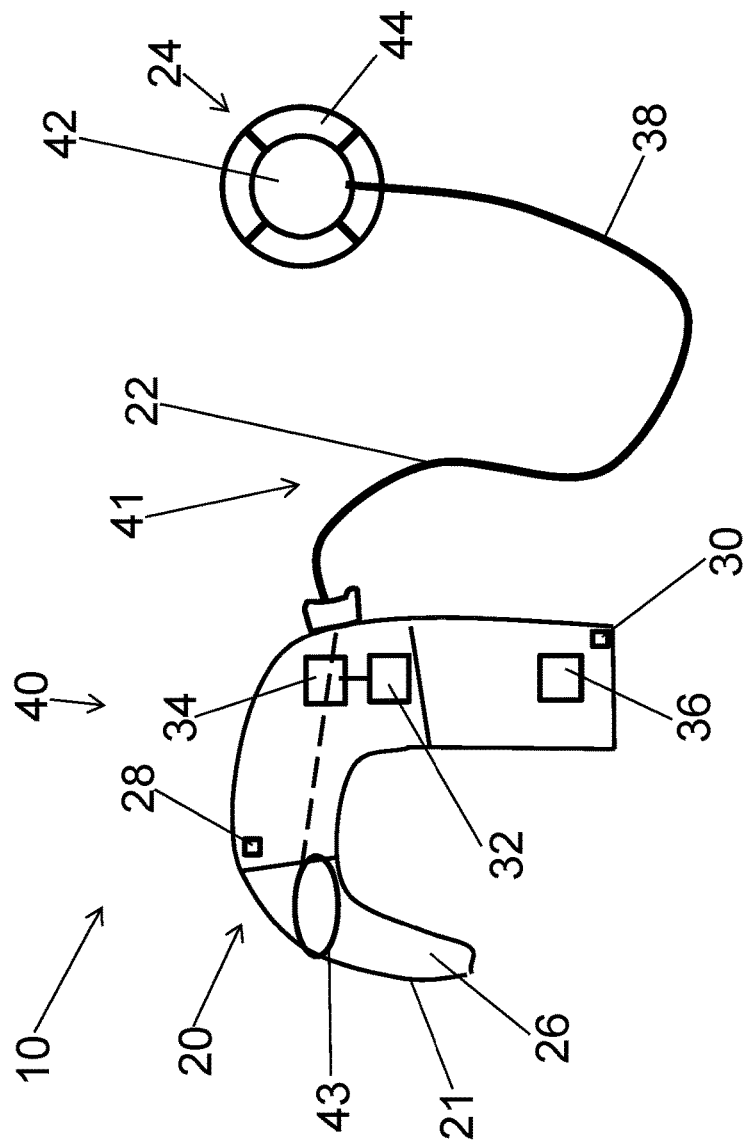
FIG. 6 illustrates a hearing device.

FIG. 6 illustrates a hearing device 10. The hearing device 10 of FIG. 6 is almost identical to the hearing device presented in FIG. 5 with the only difference that the loop antenna arranged in the hook 26 has a different orientation, i.e., it is rotated by 90 degrees.

Figure 7:
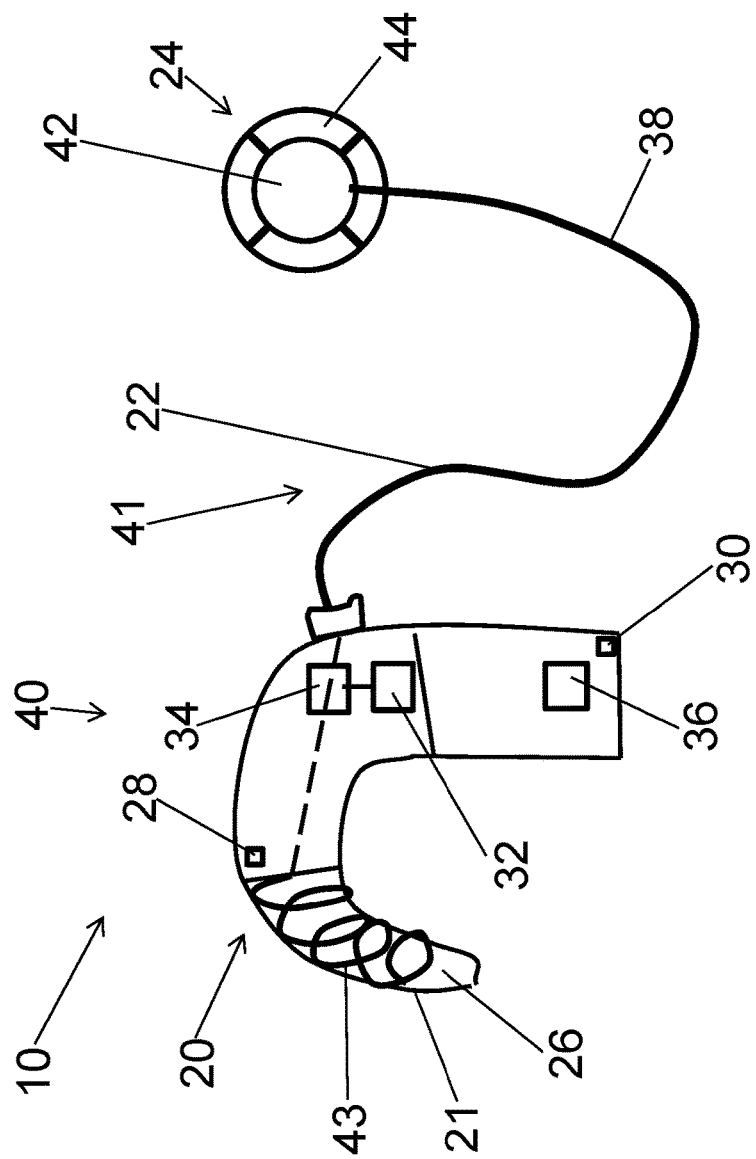
FIG. 7 illustrates a hearing device.

FIG. 7 illustrates a hearing device 10. The hearing device 10 of FIG. 7 is similar to the the hearing device 10 presented in FIGS. 4 and 5. The main difference of the hearing device 10 of FIG. 7 compared to the hearing device 10 of FIGS. 4 and 5 is that the part of the second antenna 40 arranged in the behind-the-ear part 20 is a spiral antenna, i.e., the second part 43 of the second antenna 40 is formed as a spiral antenna. Here the spiral antenna is particularly formed as a conic spiral, i.e., it corresponds to a three dimensional curve that turns around an axis at a continuously varying distance while moving parallel to the axis. The form/shape of the spiral can also be an Archimedean spiral or a helix, i.e., the spiral can be a curve that winds around a fixed center point at a increasing or decreasing distance from the point or it can be a three dimensional curve that turns around an axis at a constant distance while moving parallel to the axis. In particular the second part 43 of the second antenna 40 is arranged in hook 26. The spiral antenna allows for a relatively long antenna while no excessive length of the hook 26 is required. For example the spiral antenna can be longer than a straight wire antenna.

Alternatively, loop and spiral antennas could be combined with antennas that resemble a monopole or wire antenna which has a form that depends on a desired radio frequency. Hence the hearing device 10 could this case have multiple different antennas as second part 43 of the second antenna 40 arranged in the behind-the-ear part 20 of the hearing device 10 (not shown). E.g. for establishing a diversity antenna system or any other purpose.

Figure 8:
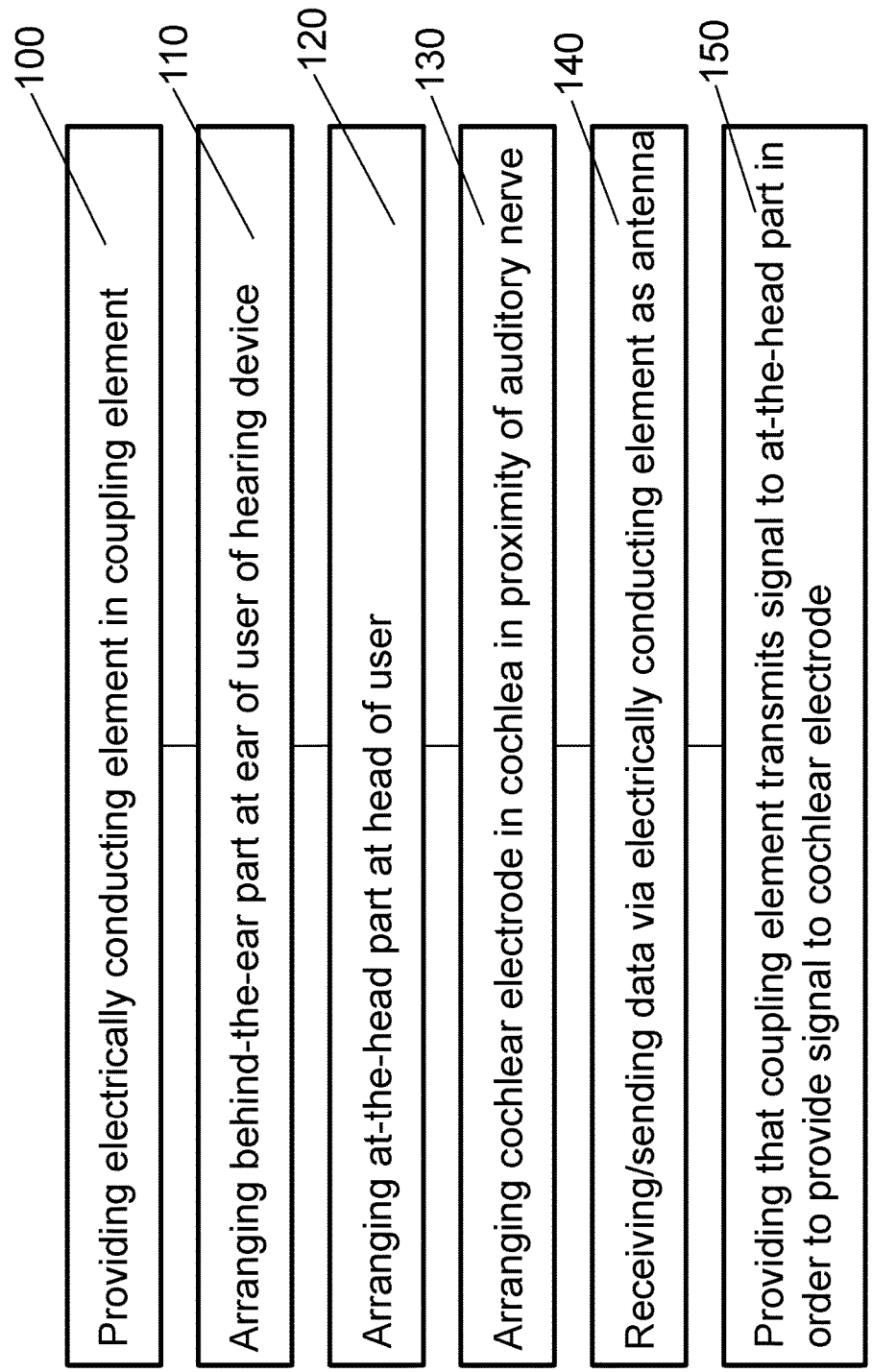
FIG. 8 illustrates a flow chart of a method.

FIG. 8 illustrates a flow chart of a method for a wireless receiving and/or sending of data in a hearing device. The hearing device comprises a coupling element, a behind-the-ear part, an at-the-head part, a second antenna, and a wireless interface. The coupling element couples the behind-the-ear part and the at-the-head part of the hearing device. The behind-the-ear part is adapted to provide a low frequency signal comprising audio. The at-the-head part includes a first antenna adapted to communicate with an implant part comprising at least one cochlear electrode adapted for converting the low frequency signal comprising audio to an output signal receivable by a user as sound. The second antenna is adapted for communicating at high frequency with an external unit. The wireless interface is adapted for receiving and/or sending data via the second antenna. The method comprises the steps:

100 providing an electrically conducting element in the coupling element,

110 arranging the behind-the-ear part at an ear of a user of the hearing device,

120 arranging the at-the-head part at the head of the user,

130 arranging the at least one cochlear electrode in the cochlea in proximity of an auditory nerve of the user,

140 receiving and/or sending data via said electrically conducting element serving as at least a part of the second antenna, and 150 providing that the coupling element transmits the signal comprising audio to the at-the-head part in order to provide the signal comprising audio to the cochlear electrode.

Figure 9:
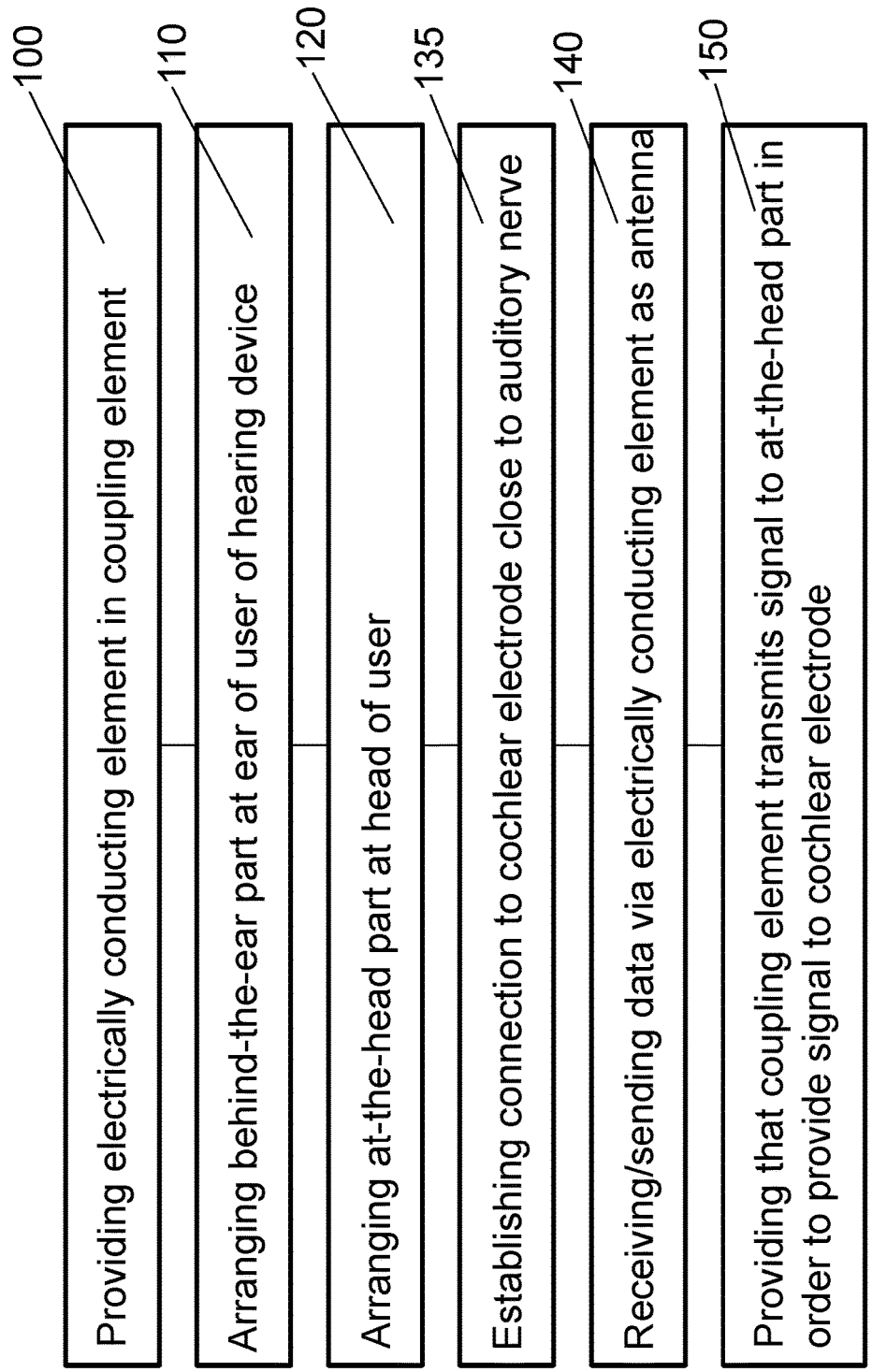
FIG. 9 illustrates a flow chart of a method.

FIG. 9 illustrates a flow chart of a method for a wireless receiving and/or sending of data in a hearing device. The hearing device of FIGS. 8 and 9 are identical. The method of FIG. 9 comprises the steps:

100 providing an electrically conducting element in the coupling element,
110 arranging the behind-the-ear part at an ear of a user of the hearing device,
120 arranging the at-the-head part at the head of the user,
135 establishing a connection to the at least one cochlear electrode in the cochlea in proximity of an auditory nerve of the user,
140 receiving and/or sending data via said electrically conducting element serving as at least a part of the second antenna, and
150 providing that the coupling element transmits the signal comprising audio to the at-the-head part in order to provide the signal comprising audio to the cochlear electrode.

Hence in contrast to the method according to FIG. 8 the at least one cochlear electrode is already arranged in the cochlea in proximity of an auditory nerve of the user. In the method according to FIG. 9 of the disclosure thus a connection to a pre-implanted cochlear electrode is established in step 135.

In an aspect, the functions or methods may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above, in the description of FIGS. 8 and 9 and in the claims.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium. In particular the steps 135, 140, and 150 of the methods described herein may be implemented in software.

In an aspect, a data processing system comprises a processor adapted to execute the computer program for causing the processor to perform at least some (such as a majority or all) of the steps of the method described above and in the claims. In particular the steps 135, 140, and 150 of the methods as disclosed in this disclosure may be implemented in software.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

REFERENCE SIGNS 10, 10' hearing device
12 binaural hearing device system
14 user
16 head of the user
18, 18' ear
20, 20' behind-the-ear part
22, 22' coupling element
24, 24' at-the-head part
26 hook
28 front microphone
30 back microphone
32 wireless interface
34 electric circuitry
36 power source
37 first balanced wire
38 electrically conducting element
39 second balanced wire
40 second antenna
41 first part of the second antenna
42 first antenna
43 second part of the second antenna
44 magnet
46, 46' implant part
48 coil
50 magnet
52 lead
54 cochlear electrodes
56 cochlea
58 auditory nerves
60 brain
62 external unit
64 antenna
66 wireless signal
68 signal comprising audio
70 printed circuit board (PCB)
72 low frequency signal connections
74 high frequency signal connections
76 balun
78 high-pass filter
80 low-pass filter 81 ground connection
82 first capacitor
83 second capacitor The present disclosure include the following general items:

1. A hearing device comprising:
a behind-the-ear part adapted for being arranged at an ear of a user and for providing a low frequency signal comprising audio,
an at-the-head part adapted for being arranged at the head of the user, wherein the at-the-head part includes a first antenna adapted to communicate with an implant part comprising at least one cochlear electrode adapted for being arranged in the cochlea in proximity of an auditory nerve of the user,
a coupling element coupling the behind-the-ear part and the at-the-head part, wherein the coupling element is adapted for transmitting the low frequency signal comprising audio to the at-the-head part,
a second antenna for communicating at high frequency with an external unit, and
a wireless interface for receiving and/or sending data via the second antenna,
the at-the-head part being adapted for providing the low frequency signal comprising audio to the at least one cochlear electrode and the at least one cochlear electrode being adapted for converting the low frequency signal comprising audio to an output signal perceivable by a user as sound,
wherein the coupling element comprises an electrically conducting element coupled to the wireless interface, the electrically conducting element is at least a part of the second antenna, and the electrically conducting element is adapted for transferring the signal comprising audio at a low frequency from the behind-the-ear part to the at-the-head part and for transmitting and/or receiving high frequency signals via the second antenna.

2. Hearing device according to item 1, wherein the at-the-head part is adapted to be magnetically coupled to the implant part at a distance from the ear of the user.

3. Hearing device according to item 1 or 2, wherein the second antenna is an electrically short antenna.

4. Hearing device according to at least one of the items 1 to 3, wherein the first antenna communicates with the implant part via mutual induction between coils of the first antenna and the implant part.

5. Hearing device according to at least one of the items 1 to 4, wherein the coupling element comprises two balanced wires for transmitting the signal comprising audio to the at-the-head part, wherein the electrically conducting element comprises the wires.

6. Hearing device according to at least one of the items 1 to 5, wherein the wireless interface is coupled to the electrically conducting element via a high-pass filter, wherein the wireless interface is coupled to the high-pass filter via a balun and wherein the high-pass filter is coupled to the wires via respective capacitors, wherein the behind-the-ear part includes a low-pass filter in the path of the signal comprising audio.

7. Hearing device according to at least one of the items 1 to 6, wherein the wireless interface is adapted for receiving and/or sending data by means of radio frequency signals in the frequency range of 1 MHz to 100 GHz, such as 300 MHz to 3 GHz, such as 2 GHz to 2.5 GHz, such as 2400 MHz to 2483.5 MHz, such as in the frequency range of 1 MHz to 200 MHz, such as 200 MHz to 400 MHz, such as 400 MHz to 800 MHz, such as 800 MHz to 1500 MHz, such as 1500 MHz to 1800 MHz, such as 1800 MHz to 2100 MHz, such as 2100 MHz to 2200 MHz, such as 2200 MHz to 2400 MHz, such as 2400 MHz to 2500 MHz, such as 2500 MHz to 2800 MHz, such as 2800 MHz to 3000 MHz, such as around 2.4 GHz, and wherein the wireless interface is optionally adapted for receiving and/or sending data according to a communication standard, such as Bluetooth.

8. Hearing device according to at least one of the items 1 to 7, wherein the electrically conducting element constitutes a first part of the second antenna and at least a second part of the second antenna is arranged in the behind-the-ear part, and a feed point to the second antenna is between the first and second part of the second antenna.

9. Hearing device according to item 8, wherein the behind-the-ear part comprises a casing which is at least partly formed as a hook with a hollow inner space and wherein the second part of the second antenna arranged in the behind-the-ear part is at least partly arranged in the hollow inner space of the hook.

10. Hearing device according to item 8 or 9, wherein at least a part of the second antenna arranged in the behind-the-ear part has a radiation pattern resembling a monopole or wire antenna which has a form that depends on a desired radio frequency.

11. Hearing device according to at least one of the items 8 to 10, wherein at least a part of the second antenna arranged in the behind-the-ear part is a loop antenna or at least a part of the second antenna arranged in the behind-the-ear part is a spiral antenna.

12. Hearing device according to at least one of the items 9 to 11, wherein the part of the second antenna arranged in the behind-the-ear part is coupled to the wireless interface via a balun or a matching network which is adapted to tune the second antenna to a desired radio frequency.

13. A method for a wireless receiving and/or sending of data in a hearing device comprising
a coupling element coupling a behind-the-ear part and an at-the-head part of the hearing device, the behind-the-ear part for providing a low frequency signal comprising audio and the at-the-head part including a first antenna adapted to communicate with an implant part comprising at least one cochlear electrode adapted for converting the low frequency signal comprising audio to an output signal receivable by a user as sound, and
a second antenna for communicating at high frequency with an external unit, and
a wireless interface for receiving and/or sending data via the second antenna,
and the method comprising the steps of:
providing an electrically conducting element in the coupling element,
arranging the behind-the-ear part at an ear of a user of the hearing device,
arranging the at-the-head part at the head of the user,
arranging the at least one cochlear electrode in the cochlea in proximity of an auditory nerve of the user,
receiving and/or sending data via said electrically conducting element serving as at least a part of the second antenna, and
providing that the coupling element transmits the signal comprising audio to the at-the-head part in order to provide the signal comprising audio to the cochlear electrode.

14. Use of a hearing device according to at least one of the items 1 to 12.

15. Use according to item 14 to wirelessly communicate with an external unit, such as another hearing device.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A hearing aid device configured to communicate with an implant part comprising at least one cochlear electrode adapted for being arranged in the cochlea in proximity of an auditory nerve of the user, the hearing aid device comprising:
    a behind-the-ear part adapted for being arranged at an ear of a user and for providing a low frequency signal comprising audio,
    an at-the-head part adapted for being arranged at the head of the user,
    an inductive coupler adapted to inductively communicate with the implant part, the inductive coupler being arranged in the at-the-head-part,
    a coupling element coupling the behind-the-ear part and the at-the-head part, wherein the coupling element is adapted for transmitting the low frequency signal comprising audio to the at-the-head part, the coupling element comprising an electrically conducting element configured to transfer the signal comprising audio at a low frequency from the behind-the-ear part to the at-the-head part, the electrically conductive element being further configured to act as an antenna for communicating at high frequency with an external unit, and
    a wireless interface for receiving and/or sending data via a high frequency carrier signal via the antenna,
    the at-the-head part being adapted for providing the low frequency signal comprising audio to the at least one cochlear electrode and the at least one cochlear electrode being adapted for converting the low frequency signal comprising audio to an output signal perceivable by a user as sound,
    wherein the behind-the-ear part filters electrical signals from the coupling element so that the high frequency parts do not enter signal processing components establishing the signal comprising audio.

2. Hearing aid device according to claim 1, wherein the at-the-head part is adapted to be magnetically coupled to the implant part at a distance from the ear of the user.

3. Hearing aid device according to claim 1, wherein the antenna is an electrically short antenna.

4. Hearing aid device according to the claim 1, wherein the coupling element comprises two balanced wires for transmitting the signal comprising audio to the at-the-head part, wherein the electrically conducting element comprises the wires.

5. Hearing aid device according to claim 1, wherein the wireless interface is coupled to the electrically conducting element via a high-pass filter, wherein the wireless interface is coupled to the high-pass filter via a balun and wherein the high-pass filter is coupled to the wires via respective capacitors, wherein the behind-the-ear part includes a low-pass filter in the path of the signal comprising audio.

6. Hearing aid device according to the claim 1, wherein the wireless interface is adapted for receiving and/or sending data by means of radio frequency signals in the frequency range of 1 MHz to 100 GHz, and wherein the wireless interface is optionally adapted for receiving and/or sending data according to a communication standard.

7. Hearing aid device according to claim 1, wherein the electrically conducting element constitutes a first part of the antenna and at least a second part of the antenna is arranged in the behind-the-ear part, and a feed point to the antenna is between the first and second part of the antenna.

8. Hearing aid device according to claim 7, wherein the behind-the-ear part comprises a casing which is at least partly formed as a hook with a hollow inner space and wherein the second part of the antenna arranged in the behind-the-ear part is at least partly arranged in the hollow inner space of the hook.

9. Hearing aid device according to claim 7, wherein at least a part of the antenna arranged in the behind-the-ear part has a radiation pattern resembling a monopole or wire antenna which has a form that depends on a desired radio frequency.

10. Hearing aid device according to claim 7, wherein at least a part of the antenna arranged in the behind-the-ear part is a loop antenna or at least a part of the antenna arranged in the behind-the-ear part is a spiral antenna.

11. Hearing aid device according to claim 8, wherein the part of the antenna arranged in the behind-the-ear part is coupled to the wireless interface via a balun and/or a matching network which is adapted to maximize the energy transfer to the antenna at a desired radio frequency.

12. A hearing aid system comprising:
    a behind-the-ear part adapted for being arranged at an ear of a user and for providing a signal comprising audio,
    an at-the-head part adapted for being arranged at a location on the head of the user, wherein the at-the-head part includes an inductive coupler adapted to inductively communicate with an implant part comprising at least one cochlear electrode adapted for being arranged in the cochlea of the user in proximity of an auditory nerve of the user,
    a mechanical coupling element mechanically coupling the behind-the-ear part and the at-the-head part, wherein the coupling element comprises an electrically conductive element configured to transfer the signal comprising audio from the behind-the-ear part to the at-the-head part,
    wherein the electrically conductive element is further configured to act as a high frequency antenna to transmit and/or receive electromagnetic signals at high frequency, and
    a wireless interface for receiving and/or sending data via a high frequency carrier signal via the high frequency antenna,
    wherein the behind-the-ear part filters electrical signals from the coupling element so that the high frequency parts do not enter signal processing components establishing the signal comprising audio.

13. The hearing aid system according to claim 12, wherein the behind-the-ear part comprises a hook configured to be grip the pinna of the user, the hook having a hollow space wherein at least part of the high frequency antenna is positioned.

14. The hearing aid system according to claim 12, wherein the behind-the-ear part further comprises an input transducer for providing the signal comprising audio.

15. A method for a wireless receiving and/or sending of data in a hearing device comprising
a coupling element coupling a behind-the-ear part and an at-the-head part of the hearing device, the coupling element comprising an electrically conducting element configured to transfer a low frequency signal comprising audio from the behind-the-ear part to the at-the-head part, the at-the-head part including an inductive coupler adapted to inductively communicate with an implant part comprising at least one cochlear electrode adapted for converting the low frequency signal comprising audio to an output signal receivable by a user as sound, and
an antenna for communicating at high frequency with an external unit, the electrically conducting element be configured to act as the antenna, and
a wireless interface for receiving and/or sending data via a high frequency carrier signal via the antenna,
and the method comprising the steps of:
providing the electrically conducting element in the coupling element,
arranging the behind-the-ear part at an ear of a user of the hearing device,
arranging the at-the-head part at the head of the user,
arranging the at least one cochlear electrode in the cochlea in proximity of an auditory nerve of the user,
receiving and/or sending data via said electrically conducting element serving as at least a part of the antenna,
providing that the coupling element transmits the signal comprising audio to the at-the-head part, and
providing that the inductive coupler of the at-the-head part inductively communicate with the implant part in order to provide the signal comprising audio to the cochlear electrode,
wherein the method further comprises, in the behind-the-ear part, filtering electrical signals from the coupling element so that the high frequency parts do not enter signal processing components establishing the signal comprising audio.

16. A method for a wireless receiving and/or transmitting of data in a hearing aid device comprising:
a coupling element coupling a behind-the-ear part and an at-the-head part of the hearing device, the coupling element comprising an electrically conducting element configured to transfer a low frequency signal comprising audio from the behind-the-ear part to the at-the-head part, the at-the-head part including an inductive coupler adapted to inductively communicate with an implant part comprising at least one cochlear electrode adapted for converting the signal comprising audio to an output signal receivable by a user as sound, and
wherein the electrically conductive element is further configured to act as a high frequency antenna for communicating at high frequency with an external unit, and
a wireless interface for receiving and/or sending data via a high frequency carrier via the antenna,
and the method comprising the steps of:
arranging the behind-the-ear part at an ear of a user of the hearing device,
arranging the at-the-head part at the head of the user,
receiving and/or sending data via said electrically conducting element serving as at least a part of the antenna,
providing that the coupling element transmits the signal comprising audio to the at-the-head part, and
providing that the inductive coupler of the at-the-head part inductively communicate with the implant part in order to provide the signal comprising audio to the cochlear electrode, wherein the method further comprises:
in the behind-the-ear part, filtering electrical signals from the coupling element so that the high frequency parts do not enter signal processing components establishing the signal comprising audio.

17. A method for a wireless receiving and/or transmitting of data in a hearing aid device comprising:
a coupling element coupling a behind-the-ear part and an at-the-head part of the hearing device, the coupling element comprising an electrically conducting element configured to transfer a low frequency signal comprising audio from the behind-the-ear part to the at-the-head part, the at-the-head part including an inductive coupler adapted to inductively communicate with an implant part comprising at least one cochlear electrode adapted for converting the signal comprising audio to an output signal receivable by a user as sound, and
wherein the electrically conductive element is further configured to act as a high frequency antenna for communicating at high frequency with an external unit, and
a wireless interface for receiving and/or sending data via a high frequency carrier via the antenna,
and the method comprising the steps of:
arranging the behind-the-ear part at an ear of a user of the hearing device,
arranging the at-the-head part at the head of the user,
receiving and/or sending data via said electrically conducting element serving as at least a part of the antenna,
providing that the coupling element transmits the signal comprising audio to the at-the-head part, and
providing that the inductive coupler of the at-the-head part inductively communicate with the implant part in order to provide the signal comprising audio to the cochlear electrode, wherein the method further comprises:
during transmission at high frequencies and audio signals, mixing signal from the wireless interface and the signal comprising audio so as to establish a composite signal in the coupling element.

18. A hearing aid device configured to communicate with an implant part comprising at least one cochlear electrode adapted for being arranged in the cochlea in proximity of an auditory nerve of the user, the hearing aid device comprising:
a behind-the-ear part adapted for being arranged at an ear of a user and for providing a low frequency signal comprising audio,
an at-the-head part adapted for being arranged at the head of the user, an inductive coupler adapted to inductively communicate with the implant part, the inductive coupler being arranged in the at-the-head-part,
a coupling element coupling the behind-the-ear part and the at-the-head part, wherein the coupling element is adapted for transmitting the low frequency signal comprising audio to the at-the-head part, the coupling element comprising an electrically conducting element configured to transfer the signal comprising audio at a low frequency from the behind-the-ear part to the at-the-head part, the electrically conductive element being further configured to act as an antenna for communicating at high frequency with an external unit, and
a wireless interface for receiving and/or sending data via a high frequency carrier signal via the antenna,
the at-the-head part being adapted for providing the low frequency signal comprising audio to the at least one cochlear electrode and the at least one cochlear electrode being adapted for converting the low frequency signal comprising audio to an output signal perceivable by a user as sound,
wherein, during transmission at high frequencies and audio signals, the behind-the-ear part mixes signal from the wireless interface and the signal comprising audio so as to establish a composite signal in the coupling element.

19. A hearing aid system comprising:
a behind-the-ear part adapted for being arranged at an ear of a user and for providing a signal comprising audio,
an at-the-head part adapted for being arranged at a location on the head of the user, wherein the at-the-head part includes an inductive coupler adapted to inductively communicate with an implant part comprising at least one cochlear electrode adapted for being arranged in the cochlea of the user in proximity of an auditory nerve of the user,
a mechanical coupling element mechanically coupling the behind-the-ear part and the at-the-head part, wherein the coupling element comprises an electrically conductive element configured to transfer the signal comprising audio from the behind-the-ear part to the at-the-head part,
wherein the electrically conductive element is further configured to act as a high frequency antenna to transmit and/or receive electromagnetic signals at high frequency, and
a wireless interface for receiving and/or sending data via a high frequency carrier signal via the high frequency antenna,
wherein, during transmission at high frequencies and audio signals, the behind-the-ear part mixes signal from the wireless interface and the signal comprising audio so as to establish a composite signal in the coupling element.

20. A method for a wireless receiving and/or sending of data in a hearing device comprising
a coupling element coupling a behind-the-ear part and an at-the-head part of the hearing device, the coupling element comprising an electrically conducting element configured to transfer a low frequency signal comprising audio from the behind-the-ear part to the at-the-head part, the at-the-head part including an inductive coupler adapted to inductively communicate with an implant part comprising at least one cochlear electrode adapted for converting the low frequency signal comprising audio to an output signal receivable by a user as sound, and
an antenna for communicating at high frequency with an external unit, the electrically conducting element be configured to act as the antenna, and
a wireless interface for receiving and/or sending data via a high frequency carrier signal via the antenna,
and the method comprising the steps of:
providing the electrically conducting element in the coupling element,
arranging the behind-the-ear part at an ear of a user of the hearing device,
arranging the at-the-head part at the head of the user,
arranging the at least one cochlear electrode in the cochlea in proximity of an auditory nerve of the user,
receiving and/or sending data via said electrically conducting element serving as at least a part of the antenna,
providing that the coupling element transmits the signal comprising audio to the at-the-head part, and
providing that the inductive coupler of the at-the-head part inductively communicate with the implant part in order to provide the signal comprising audio to the cochlear electrode,
wherein the method further comprises, during transmission at high frequencies and audio signals, mixing signal from the wireless interface and the signal comprising audio so as to establish a composite signal in the coupling element.

* * * * *